United States Patent [19]

Saito et al.

[11] Patent Number: 4,871,868

[45] Date of Patent: Oct. 3, 1989

[54] PRODUCTION OF SUBSTITUTED ACETYLENIC COMPOUNDS

[75] Inventors: Yuzuru Saito, Takatsuki; Kokichi Yoshida, Suita, both of Japan

[73] Assignee: Takeda Chemical Industries, Ltd., Osaka, Japan

[21] Appl. No.: 163,849

[22] Filed: Mar. 3, 1988

[30] Foreign Application Priority Data

Mar. 11, 1987 [JP] Japan .................................. 62-56371

[51] Int. Cl.⁴ .................. C07D 309/12; C07C 33/042; C07C 57/18
[52] U.S. Cl. ...................................... 549/416; 558/55; 562/598; 568/873; 568/812; 568/813; 568/687; 585/505; 260/405.5
[58] Field of Search ........................ 549/416; 562/598; 568/873, 812, 813, 687; 585/505; 260/405.5

[56] References Cited

U.S. PATENT DOCUMENTS 4,571,438 2/1986 Byers et al. .......................... 568/420

OTHER PUBLICATIONS

Roberts et al., "Basic Principles of Organic Chemistry", W. A. Benjamins, Inc., New York, 1965, pp. 298–302.

*Primary Examiner*—Nicky Chan
*Attorney, Agent, or Firm*—Wenderoth, Lind & Ponack

[57] ABSTRACT

A method of producing substituted acetylenic compounds which comprises: reacting an organic compound having the general formula of $$A-X \qquad (I)$$

wherein A represents a saturated or unsaturated aliphatic hydrocarbon residue of 1–20 carbon atoms which may have one or more substituents inactive in the reaction, and X represents a halogen atom or an arylsulfonyloxy group, with a metal acetylide having the general formula of $$M-C\equiv C-B \qquad (II)$$

wherein M represents an alkali metal, and B represents (a) a hydrogen, (b) a saturated or unsaturated hydrocarbon residue which may have one or more substituents inactive in the reaction, or (c) a saturated or unsaturated hydrocarbon residue which has a substituent having the general formula of $$-C\equiv C-M \qquad (III)$$

wherein M represents an alkali metal, in the presence of an alkyl-2-imidazolidinone having the general formula of

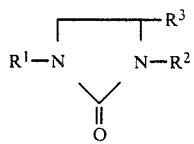
$$(IV)$$

wherein $R^1$ and $R^2$ independently represent a lower alkyl, and $R^3$ represents a hydrogen or a lower alkyl.

7 Claims, No Drawings

PRODUCTION OF SUBSTITUTED ACETYLENIC COMPOUNDS

This invention relates to a method of producing substituted acetylenic compounds, and in particular to a method of producing, in high yields and high purity and in excellent reproducibility, substituted acetylenic compounds useful as medicines or chemicals including those for agricultural use or as intermetiates for the production of these products.

There is a well known method for the production of substituted acetylenic compounds in which an organic halide such as an alkyl halide is coupled or condensed with an alkali metal acetylide at low temperatures or under high pressures in liquid ammonia, as described in, for example, "Organic Synthesis", Coll. Vol. 4, 117 (1963). It is also known that, for example, dimethylformamide (Angew. Chem., 71, 245 (1959)), hexamethylphosphoramide (Synth. Commun., 4, 199 (1974) and J. Chem. Soc. Perkin Trans. I, 1591 (1893)), dimethylsulfoxide (J. Chem. Soc. (C) 1966, 1882), and N-methylpyrrolidone (Synth. Commun., 2, 87 (1972)) are respectively useful as a reaction promoter to increase yields of products in coupling reactions.

However, since the aforesaid prior methods need in many cases reactions at low temperatures or high pressures, they need specially devised apparatus and techniques, and moreover the prior art methods are lacking in reproducibility of reactions or yields, but also the promoters or solvents used might be carcinogenic. Even if the reactions can be carried out at normal temperatures and pressures, the yields of desired substituted acetylenic compounds are usually small. In this way, the prior art methods are neither feasible nor suitable for the industrial production of substituted acetylenic compounds.

Many substituted acetylenic compounds are important as medicines or chemicals, or as intermetiates for the production of such products, as described previously. For instance, as described in Japanese Patent Laid-Open No. 56-154433 and No. 61-44840, certain quinine compounds having acetylenic substituents therein are known to be useful for medical treatment or prevention of, for example, bronchial asthma, allergic diseases, cerebral thrombosis, hypertension, ischemic deseases such as cardiac infarction, coronary insufficiency, atherosclerosis and the like.

By way of example, 2-[12-(2-tetrahydropyranyloxy)-5,10-dodecadiynyl]-1,4-dimethoxy-3,5,6-trimethylbenzene is an important intermediate for producing such quinone compounds, and is obtained by a coupling reaction of 1-(2-tetrahydropyranyloxy)-2,7-octadiyne with 2-(4-iodobutyl)-1,4-dimethoxy-3,5,6-trimethylbenzene. However, the above reaction gives the coupling product in small yields, and the yield is about 70% at most even in the presence of a hexamethylphosphoramide promoter (J. Chem. Soc., Perkin Trans. I, 1591 (1983)).

Again with regard to promoters, it is described in U.S. Pat. No. 4,540,826 and No. 4,571,438 both to D. S. Banasiak et al. that 1,3-dimethyl-2-imidazolidinone, in addition to diglyme (diethylene glycol dimethyl ether), triglyme (triethylene glycol dimethyl ether), tetraglyme (tetraethylene glycol dimethyl ether), hexamethylphosphorous triamide and 1,3-dimethyl-3,4,5,6-tetrahydro-2(1H)-pyrimidinone, is said usable as a promoter in the coupling reaction of an organic α, ω-dihalide compound and a lithium acetylide to provide alkynic monohalide compound such as hexadecynyl bromide. However, no actual use of 1,3-dimethyl-2-imidazolidinoe as a promoter is reported in the literature, although the use of a variety of other promoters are described therein.

The present inventors have made an intensive investigation of coupling reactions of organic monohalide compound with a metal acetylide in the presence of a reaction promoter, and have found that an alkyl-2-imidazolidinone is especially effective in promoting the coupling reactions to provide substituted acetylenic compounds in fact in markedly high yields and reproducibility under milder reaction conditions. Further the inventors have found that the alkyl-2-imidazolidinones are similarly effective as a promoter in coupling reactions where arylsulfonates are reacted with a metal acetylide.

It is therefore an object of the invention to provide a method of producing substituted acetylenic compounds by a coupling reaction of an organic monohalide compound or an aryl sulfonate with a metal acetylide in the presence of an alkyl-2-imidazolidinone as a promoter, especially in high yields and high purity and in excellent reproducibility under mild reaction conditions.

The method of producing substituted acetylenic compounds of the invention comprises: reacting an organic compound having the general formula of $$A-X \qquad (I)$$

wherein A represents a saturated or unsaturated aliphatic hydrocarbon residue of 1–20 carbon atoms which may have one or more substituents inactive in the reaction, and X represents a halogen atom or an arylsulfonyloxy group, with a metal acetylide having the general formula of $$M-C\equiv C-B \qquad (II)$$

wherein M represents an alkali metal, and B represents (a) a hydrogen, (b) a saturated or unsaturated hydrocarbon residue which may have one or more substituents inactive in the reaction, or (c) a saturated or unsaturated hydrocarbon residue which contains a susbstituent having the general formula of $$-C\equiv C-M \qquad (III)$$

wherein M represents an alkali metal, in the presence of an alkyl-2-imidazolidinone having the general formula of

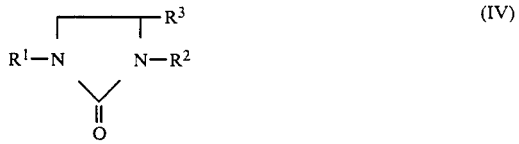

wherein $R^1$ and $R^2$ independently represent a lower alkyl, and $R^3$ represents a hydrogen or a lower alkyl.

The organic compound (I) used in the invention is an organic monohalide or an arylsulfonate. More specifically, the hydrocarbon residue A is a saturated or unsaturated aliphatic hydrocarbon residue of 1–20 carbon atoms, and includes an alkyl, an alkenyl or an alkynyl. The hydrocarbon residue A may have one or more substituents inactive in the reaction. Such substituents include, for example, halogen, hydroxyl, acetal, carboxyl, alkoxy, aryloxy, alkoxycarbonyl, aryloxycarbonyl, acyloxy, aroyloxy, carbamoyl, N-substituted carbamoyl, cyano, aryl and cycloalkyl. Therefore, when the hydrocarbon residue A has a halogen as a substituent, the halogen must be less reactive in the coupling reaction than the halogen X of the compound (I). More specifically, it is preferred that the haogen as a substituent of the compound (I) be substantially inactive in the coupling reaction. Namely, when the halogen X is I or Br, the halogen as a substituent on the compound (I) is Cl or F.

Organic monobromides or monoiodides which additionally have Cl or F as a substituent can be deemed monohalide compounds in the invention since the halogen Br or I only is substantially reactive to metal acetylides in the coupling reaction of the invention.

When the hydrocarbon residue A has an acetal group, the acetal group is advantageously a cyclic acetal such as a tetrahydropyranyloxy or a tetrahydrofuryloxy group. Further when the hydrocarbon residue A contains an alkoxy, an aryloxy, an alkoxycarbonyl, an aryloxycarbonyl, acyloxy or aroyloxy, the number of the carbon atoms in the alkoxy or acyloxy group is preferably in the range of from 1 to 3, while the number of the carbon atoms in the aryl or aroyloxy group is preferably in the range of from 6 to 10. N-Substituted carbamoyl group may be N-methyl-, N-ethyl-, N,N-dimethyl- or N,N-diethylcarbamoyl.

When the hydrocarbon residue A has an aryl or a cycloalkyl group as a substituent, the aryl or cycloalkyl group may also have such substituents as aforementioned, which include, for example, halogen, hydroxyl, acetal, alkyl, carboxyl, alkoxy, aryloxy, alkoxycarbonyl, aryloxycarbonyl, acyloxy, aroyloxy, carbamoyl, N-substituted carbamoyl, cyano, aryl and cycloalkyl. Preferred substituents may be lower aliphatic alkyl groups such as methyl or ethyl, or lower alkyloxy groups such as methoxy or ethoxy.

In the organic halide represented by the formula (I) wherein X is a halogen, the halogen is Cl, Br or I, and are preferred Br or I so that the substituted acetylenic compound is obtained in high yields by the coupling reaction thereof with a metal acetylide which will be hereinafter described.

The organic halides usable in the invention include, for example, methyl iodide, ethyl bromide, ethyl iodide, n-propyl chloride, n-butyl iodide, 1-bromopentane, 1-bromo-4-chlorobutane, 3-bromo-1-propanol, 1-bromo-2-propylene, 5-iodo-1-pentyne, ethoxychloromethane, 8-bromooctanoic acid, 1-chloro-5-(2-tetrahydropyranyloxy)pentane, octyl bromide, chloromlethyl acetate, 3-bromo-1-propene, 3-bromo-1-propyne, 4-bromo-2-butenoic acid, 1-bromo-2-methoxyethane, 1-chloro-4-(2-tetrahydropyranyloxy)butane, 1-fluoro-4-iodobutane, 1-chloro-5-iodopentane, 2-bromo-1,1-diethoxyethane, 1-chloro-1-ethoxypentane, 2-chloromethyl-4-methoxy-2-butene, 1-chloromethyloxybutane, 9-bromononaoic acid, 1-bromo-2-octyne, 4-chloro-1,1-diethoxybutane, benzyl iodide, 3-chloro-2-phenyl-1-propene, 2-(4-iodobutyl)-1,4-dimethoxy-3,5,6-trimethylbenzene, 2-(4-iodobutyl)-1,4,5,6-tetramethoxy-3-methylbenzene, 2-(7-iodo-5-heptynyl)-1,4-dimethoxy-3,5,6-trimethylbenzene, and 2-(6-iodo-3-methyl-2-hexenyl)-1,4-bis(methoxymethyloxy)-3-methyl-5,6-dimethoxybenzene, However, these organic halides are mentioned for exemplification only, and the invention is not specifically limited in organic halides used.

In the aryl sulfonate represented by the formula (I) wherein X is an arylsulfonyloxy group, it is preferred that the arylsulfonyloxy group be a benzenesulfonyloxy or a p-toluenesulfonyloxy (tosyloxy) group to provide high yields of the substituted acetylenic compound by the coupling reaction of the invention. Preferred arylsulfonates usable in the invention include, for example, 4-pentyn-1-yl p-toluenesulfonate, ethyl p-toluenesulfonate, n-butyl p-toluenesulfonate, n-octyl p-toluenesulfonate, and n-octyl benzenesulfonate, although most any arylsulfonate may be usable in the invention.

In turn, in the metal acetylide (II) used in the invention, B represents (a) a hydrogen, (b) a saturated or unsaturated hydrocarbon residue which may have one or more substituents inactive in the reaction, or (c) a saturated or unsaturated hydrocarbon residue which has a susbstituent having the general formula of

$$-C\equiv C-M \quad (III)$$

wherein M represents an alkali metal. When the hydrocarbon residue B is an alkyl, an alkenyl, an alkynyl or a cycloalkyl, the number of the carbon atoms contaied therein is usually in the range of from 1 to 20, and when the hydrocarbon residue B is an aryl, the aryl group is usually composed of from 6 to 20 carbon atoms.

The hydrocarbon residue B may also have one or more substituents thereon inactive in the reaction. Such substituents include, for example, halogen, hydroxyl, acetal, carboxyl, alkoxy, aryloxy, alkoxycarbonyl, aryloxycarbonyl, acyloxy, aroyloxy, carbamoyl, N-substituted carbamoyl, and cyano. Therefore, when the hydrocarbon residue B has a halogen as a substituent, the halogen must be less reactive in the coupling reaction than the halogen X of the compound (I), and more specifically it is preferred that the halogen contained as a substituent in the hydrocarbon residue B be substantially inactive in the coupling reaction. Namely, when the halogen X of the compound (I) is I or Br, the halogen as a substituent contained in the metal acetylide (II) is Cl or F.

When the hydrocarbon residue B has an acetal group, it is advantageous that the acetal group be a cyclic acetal group such as a tetrahydropyranyloxy group or a tetrahydrofuryl group.

Further when the hydrocarbon residue B has an alkoxy, an aryloxy, an alkoxycarbonyl, an aryloxycarbonyl, acyloxy or aroyloxy, the number of the carbon atoms in the alkoxy or acyloxy group is preferably 1–3, and the number of the carbon atoms in the aryl or aroyloxy group is preferably 6–10. Further, N-substituted carbamoyl group may be N-methyl-, N-ethyl-, N,N-dimethyl- or N,N-diethylcarbamoyl.

The alkali metal M in the metal acetylide (II) is preferably Na, K or Li. The metal acetylide used in the invention can be prepared by metallation of an acetylenic compound with a metallation agent in a conventional method well known in the art. An alkali metal amide such as sodium amide or potassium amide, or an alkyl or an aryl alkali metal such as n-butyllithium cr phenyl lithium is usually used as a metallation agent. The metallation reaction is carried out usually in solvents which are exemplified by liquid ammonia; aromatic hydrocarbons such as xylene; ethers such as diethyl ether, diisopropyl ether, di-n-butyl ether, dimethoxyethane or 1,1-dimethoxyethane; or amines such as ethylenediamine, at temperatures usually in the range of from about −40° C. to about 100° C., although the temperature is not critical. One skilled in the art will be able to readily select suitable metallation agents and reaction conditions including solvents and reaction temperatures. The metal acetylide thus prepared may be used without purification or isolation in the coupling reaction of the invention.

The alkali metal acetylides usable in the invention include those of, for example, alkynes such as acetylene, 1-hexyne, 1-undecyne, 1-pentene-3-yne, 3-heptene-1-yne, 1-octyne, phenylacetylene, 5-ethynyl-2-methylpyridine, or 1,7-octadiyne; alkynic alcohols such as 7-octyne-1-ol, 2-phenyl-2-hydroxy-3-butyne, 3-butyne-1-ol, 4-pentyne-1-ol, 4-methyl-4-hydroxy-1-pentyne, 2-propyne-1-ol, or 3-hydroxy-3-methyl-4-pentyne; acetals of alkynic alcohols such as 1-(2-tetrahydropyranyloxy)-2-propyne, 1-(2-tetrahydropyranyloxy)-2,7-octadiyne, or 1-(2-tetrahydropyranyloxy)-4,6-heptadiyne; alkynic carboxylic acids such as 6-heptynoic acid, 7-octynoic acid, or 9-decynoic acid; alkynic halides such as 1-chloro-4-pentyne; and others such as 5-benzoyl-1-pentyne.

According to the invention, the coupling reaction of the organic compound (I) with the metal acetylide (II) is carried out in the presence of an alkyl-2-imidazolidinone having the general formula of

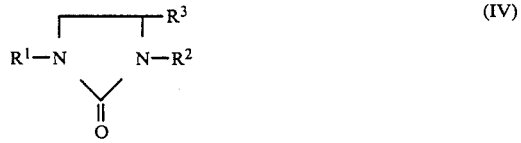

wherein $R^1$ and $R^2$ independently represent a lower alkyl, and $R^3$ represents a hydrogen or a lower alkyl. When $R^1$, $R^2$ or $R^3$ is a lower alkyl, it is preferably an alkyl of 1–3 carbons such as methyl, ethyl or propyl. Therefore, preferred examples of the alkyl-2-imidazolidinones used in the invention include 1,3-dimethyl-2-imidazolidinone, 1,3-diethyl-2-imidazolidinone, 1,3-diisopropyl-2-imidazolidinone and 1,3,4-trimethyl-2-imidazolidinone.

In the invention, the alkyl-2-imidazolidinones are either used singly as a solvent at the same time, or used together with other organic solvents. As such organic solvents there may be used ethers such as tetrahydrofuran, dioxane or diethyl ether; saturated aliphatic or alicyclic hydrocarbons such as hexane, heptane, cyclopentane or cyclohexane; aromatic hydrocarbons such as benzene, toluene or xylene; or primary, secondary or tertiary amines such as ethylamine, diethylamine, triethylamine or pyridine. Further, the alkyl-2-imidazolidinones may be used together with known promoters such as dimethylformamide, hexamethylphosphoramide, dimethylsulfoxide or N-methylpyrrolidone.

The coupling reaction of the aforesaid compound (I) with the metal acetylide (II) may be carried out under an inert gas atomosphere such as helium, nitrogen or argon. The reaction temperature is usually in the range of from −20° C. to 150° C., with from 0° C. to 70° C. preferred, although the temperature is not critical.

The metal acetylide (II) is used usually in amounts of not less than 0.5 times, preferably in amounts of about 1 to 2 times as much as the theoretical amount required in the reaction, although an optimum amount is rather dependent on the substituents contained in the metal acetylide used.

After the coupling reaction, ammonium chloride or alcohols, for instance, are added to the resultant reaction mixture to decompose the unreacted metal acetylide, and then the objective substituted acetylenic compound can be isolated and purified by known methods such as extraction, phase separation, distillation or chromatography. If necessary, the resultant acetylenic compound, without separation from the reaction mixture or purification, may be used in a further coupling reactions. On the other hand, the alkyl-2-imidazolidinone used in the reaction can be readily recovered from an aqueous layer by extraction thereof with, for example, methylene chloride, after the extraction of the resultant substituted acetylenic compound from the reaction mixture.

The invention will be more fully understood with reference to the following examples.

EXAMPLE 1

Sodium amide (23.4 g, 0.6 mole) was added to tetrahydrofuran (240 ml) under an argon atmosphere, and then to the sodium amide was added dropwise a tetrahydrofuran (249 ml) solution of 1-(2-tetrahydropyranyloxy)-2-propyne (78.5 g, 0.56 mole) below 35° C. over a period of about 30 minutes. Then the mixture was heated to about 50° C. and stirred for about 1 hour. After cooling to about 0° C., 1,3-dimethyl-2-imidazolidinone (200 ml) was added to the reaction mixture.

While keeping the above reaction mixture at 0° C., there was added dropwise thereto a tetrahydrofuran (200 ml) solution of 5-iodo-1-pentyne (77.6 g, 0.40 mole) over about 40 minutes, and then the mixture was stirred at the same temperature for about another 1 hour.

The resultant reaction mixture was maintained at temperatures of not more than about 25° C., there was added thereto a saturated aqueous solution (200 ml) of ammonium chloride, and then the mixture was extracted with ethyl acetate (500 ml). The organic layer was separated with a separatory funnel, and washed twice with water (300 ml). The ethyl acetate was removed by distillation under reduced pressures, and the residual was distilled under reduced pressures to provide 1-(2-tetrahydropyranyloxy)-2,7-octadiyne (75.9 g, 0.37 mole) as a fraction of bp. 107°–112° C./0.3 mmHg. The theoretical yield was 92% based on 5-iodo-1-pentyne used.

EXAMPLE 2

Sodium amide (20.0 g, 0.5 mole) and 1-(2-tetrahydropyranyloxy)-2,7-octadiyne (80.0 g, 0.39 mole) were added to tetrahydrofuran (200 ml) under a nitrogen atmosphere. Then the mixture was heated to about 50° C., and stirred for about 1 hour. After cooling to about 0° C., 1,3-dimethyl-2-imidazolidinone (200 ml) was added to the reaction mixture.

While keeping the above reaction mixture at 0° C., there was added dropwise thereto a tetrahydrofuran (100 ml) solution of 2-(4-iodobutyl)-1,4-dimethoxy-3,5,6-trimethylbenzene (100.0 g, 0.28 mole) over about 30 minutes, and then the mixture was stirred at the same temperature for about another 1 hour.

The resultant reaction mixture was maintained at temperatures of not more than about 25° C., and there was added thereto a saturated aqueous solution (200 ml) of ammonium chloride, and then water (400 ml) and ethyl acetate (600 ml). The organic layer was separated with a separatory funnel, and washed twice with water (400 ml). The ethyl acetate was removed by distillation under reduced pressures, and the residual liquid was distilled under reduced pressures to provide an oily residue (154.8 g).

The oily material was analyzed by high performance loquid chromatography (with a column iof Nucleosil 5C18 by Gaschro Kogyo K.K., Japan; detected by refractive index detector), to illustrate that the main components therein were 2-[12-(2-tetrahydropyranyloxy)-5,10-dodecadiynyl]-1,4-dimethoxy-3,5,6-trimethylbenzene, and that the content thereof in the oily material was 74.0%. Accordingly, the yield was 114.6 g (0.26 mole) in terms of 100% purity compounds, and the theoretical yield was 94% based on 2-(4-iodobutyl)-1,4-dimethoxy-3,5,6-trimethylbenzene used.

The oily material (70.0 g, or 51.8 g as 100% purity compounds) was chromatographed on silica gel (600 g of BW-820 by Fuji Davison K.K., Japan) employing isopropyl ether/n-hexane (⅓ volume ratio, 6 l) and isopropyl ether/n-hexane (1/1 volume ratio, 2.5 l) as eluants in this sequence. The eluates were collected and the solvent was removed by distillation under reduced pressures to provide 2-[12-(2-tatrahydropyranyloxy)-5,10-dodecadiynyl]-1,4-dimethoxy-3,5,6-trimethylbenzene (50.8 g). The chromatographic purification yield was 98%.

REFERENCE EXAMPLE

The oily material (68.0 g, or 50.3 g, 0.11 mole as 100% purity compound) was dissolved in an aqueous acetonitrile solution (prepared by mixing 175 ml of acetonitrile with 75 ml of water). While keeping the solution at about 0° C., there was dropwise added thereto cerium (IV) ammonium nitrate (145 g, 0.26 mole) in aqueous acetonitrile (prepared by mixing 125 ml of aceetonitrile with 125 ml of water) over a period of about 1 hour, and then stirred for another 30 minutes period.

The acetonitrile was removed by distillation under reduced pressures. To the residual liquid were added isopropyl ether (250 ml) and water (200 ml), and the organic layer was separated with a separatory funnel, and washed twice with water (200 ml). The isopropyl ether was removed by distillation under reduced pressures to give an oily material (59.8 g).

Methanol (300 ml) was added to the oily material, and then p-toluenesulfonic acid monohydrate (1.8 g) was added as a catalyst, followed by stirring for about 1 hour under refluxing. The resultant reaction mixture was cooled to below 25° C., and was added thereto an 8 W/V % aqueous solution (20 ml) of sodium hydrogen carbonate, followed by distillation under reduced pressures to remove the methanol.

Isopropyl ether (200 ml) and water (200 ml) were added to the resultant residual, and the solution was extracted. The organic layer was separated, and washed twice with water (200 ml), and the isopropyl ether was removed by distillation under reduced pressures to give an oily residual (49.5 g).

The oily residue (49.5 g) was dissolved in isopropyl ether/n-hexane (⅓ volume ratio, 15 ml), and the solution was chromatographed on silica gel (300 g of BW-820 Fuji Davison K.K., Japan) employing isopropyl ether/n-hexane (1/1 volume ratio, 2 l) and isopropyl ether (1.5 l) as eluants in this sequence. The eluates were collected and distilled under reduced pressures to remove the solvents, to provide an oily material (38.3 g).

The oily material (38.3 g) was dissolved in ethyl acetate/n-hexane (1/1 volume ratio, 400 ml) and warmed to 35° C. to dissolve the material therein. The cooling to 5° C. of the solution with stirring for about 1 hour, so that yellow needle crystals precipitated out, which were collected by filtration, and dried, to provide 2-(12-hydroxy-5,10-dodecadiynyl)-3,5,6-trimethyl-1,4-benzoquinone (34.7 g). The theoretical yield was 93% based on 2-[12-(2-tatrahydropyranyloxy)-5,10-dodecadiynyl]-1,4-dimethoxy-3,5,6-trimethylbenzene used.

COMPARATIVE EXAMPLE 1

Employing hexamethylphosphoramide (200 ml) in place of 1,3-dimethyl-2-imidazolidinone, and otherwise in the same manner as in Example 1, the reaction was carried out, to give 1-(2-tetrahydropyranyloxy)-2,7-octadiyne in a theoretical yield of 45% based on 5-iodo-1-pentyne used.

COMPARATIVE EXAMPLES 2-11

Employing a variety of promoters (200 ml each) as shown in Table 1 in place of 1,3-dimethyl-2-imidazolidinone, the reaction was carried out otherwise in the same manner as in Example 2, to provide oily materials, and the materials were analyzed in the same method as in Example 2.

The theoretical yields of 2-[12-(2-tatrahydropyranyloxy)-5,10-dodecadiynyl]-1,4-dimethoxy-3,5,6-trimethylbenzene based on 2-(4-iodobutyl)-1,4-dimethoxy-3,5,6-trimethylbenzene used were shown in Table 1.

TABLE 1

| Comparative Examples | Promoters | Theoretical Yields (%) |
|---|---|---|
| 2 | Ethylenediamine | 66 |
| 3 | Hexamethylphosphoramide | 71 |
| 4 | N—methylpyrrolidone | 19 |
| 5 | Dimethylformamide | 24 |
| 6 | Dimethylsulfoxide | 18 |
| 7 | Diglyme | 18 |
| 8 | Triglyme | 12 |
| 9 | Tetraglyme | 9 |
| 10 | Tetramethylurea | 62 |
| 11 | Tetramethylenediamine | 36 |

EXAMPLE 3

Sodium amide (4.7 g, 0.12 mole) and 1-hexyne (9.8 g, 0.12 mole) were added to tetrahydrofuran (20 ml) under a nitrogen atmosphere. The mixture was heated to about 50° C., and stirred for about 1 hour. After cooling to about 0° C., 1,3,4-trimethyl-2-imidazolidinone (30 ml) was added to the reaction mixture.

While keeping the above reaction mixture at 0° C., there was dropwise added thereto ethoxychloroethane (9.5 g, 0.1 mole) in tetrahydrofuran (20 ml) over about 30 minutes, and then the mixture was heated to about 50° C., followed by stirring for another 1.5 hours.

The resultant reaction mixture was maintained at temperatures of about 25° C., and there was added thereto a saturated aqueous solution (50 ml) of ammonium chloride, and then water (40 ml) and ethyl acetate (80 ml). The organic layer was separated with a separatory funnel, and and washed twice with water (60 ml). The ethyl acetate was removed by distillation under reduced pressures, to provide 1-ethoxy-2-heptyne (12.3 g, 0.88 mole) as a fraction of bp. 70°-74° C./20 mmHg in a theoretical yield of 88% based on ethoxychloroethane used.

EXAMPLE 4

Lithium amide (6.9 g, 0.30 mole) and 7-octyne-1-ol 12.6 g, 0.10 mole) were added to tetrahydrofuran (40 ml) under a nitrogen atmosphere. The mixture was heated to about 40° C., and stirred for about 1 hour. After cooling to about 0° C., 1,3,4-trimethyl-2-imidazolidinone (50 ml) was added to the reaction mixture.

While keeping the above reaction mixture at 0° C., there was dropwise added thereto 8-bromo-1-octanoic acid (11.2 g, 0.05 mole) in tetrahydrofuran (30 ml) over about 30 minutes, and then the mixture was heated to about 40° C., followed by stirring for another 2 hours.

The resultant reaction mixture was maintained below 25° C., and there was added thereto a saturated aqueous solution (120 ml) of ammonium chloride, and then water (50 ml) and ethyl acetate (250 ml). After further addition of 2N hydrochloric acid to make the aqueous layer acidic, the mixture was extracted, and the separated organic layer was washed twice with 0.5N hydrochloric acid (80 ml).

The ethyl acetate was removed under reduced pressures, ether (30 ml) was added to the resultant residue, and the solution was cooled so that crystallization took place. The crystallines of 16-hydroxyhexadeca-9-yonic acid (11.6 g, 0.043 mole) were collected by filtration and dried. The theoretical yield was 86% based on 8-bromo-1-octanoic acid used.

EXAMPLE 5

A n-hexane solution (150 ml) of n-butyllithium (1.6 mole/l) was dropwise added to 7-octynoic acid (16.8 g, 0.12 mole) in 1,3-dimethyl-2-imidazolidinone (50 ml) under stirring and keeping the temperature of the solution below 0° C. over a period of about 1 hour under an argon atmosphere.

While keeping the above reaction mixture at 0° C., there was added dropwise thereto ethyl bromide (10.9 g, 0.10 mole) over about 1 hour. Then, the mixture was heated to about 25° C., and the reaction was carried out at the same temperature for another 15 hours.

After the reaction was completed, a saturated aqueous solution (100 ml) of ammonium chloride was added to the reaction mixture below 25° C., and then there were added water (50 ml) and ethyl acetate (25 ml). After further addition of 2N hydrochloric acid to make the aqueous layer acidic, the organic layer was separated, and washed twice with 0.5N hydrochloric acid (80 ml).

After the organic layer was dried over magnesium sulfate (0.2 g), the solvent was removed by distillation under reduced pressures. The residual liquid was distilled under reduced pressures, to provide decynoic acid (13.8 g, 0.082 mole) as a fraction of bp. 95°–98° C./0.1 mmHg in a theoretical yield of 82% based on ethyl bromide used.

EXAMPLES 6–8

Employing a variety of acetylenic compounds and organic halides shown in Table 2, the reactions were carried out at temperatures for reaction periods as shown in Table 2 otherwise in the same manner as in Example 5. The products, and their yields and boiling points are shown in Table 2.

EXAMPLE 9

While keeping the temperature below 0° C., a n-hexane solution (150 ml) of n-butyllithium (1.6 mole/l) was added dropwise to 7-octynoic acid (16.8 g, 0.12 mole) in 1,3-dimethyl-2-imidazolidinone (50 ml) under stirring over a period of about 1 hour under an argon atmosphere.

TABLE 2

| | Reactants | | | Reaction Conditions | | Results | | |
|---|---|---|---|---|---|---|---|---|
| Examples | Acetylenic Compounds (g; mole) | Reagents (g; mole) | Halides (g; mole) | Temp. (°C.) | Time (hr) | Products (g; mole) | Yields (%) | Bp. |
| 6 | 1-Hexyne (8.2; 0.10) | n-Butyllithium[1] (62.5; 0.10) | 3-Bromopropanol | 40 | 2 | 4-Nonyn-1-ol | 82 | 114–118° C./20 mmHg |
| 7 | 1-Hexyne (9.8; 0.12) | n-Butyllithium[1] (75.0; 0.12) | 1-Chloropropane | 25 | 20 | 4-Nonyne | 86 | 150–154° C./760 mmHg |
| 8 | 2-Hydroxy-2-phenyl-3-butyne (9.8; 0.12) | n-Butyllithium[1] (150.0; 0.24) | 1-Bromo-4-chlorobutane | 2 | 2 | 1-Chloro-7-hydroxy-7-phenyl-5-octyne (17.8; 0.075) | 75 | 145–150° C./0.2 mmHg |

Notes:
[1] 1.6 Mole/l n-hexane solution.

After removing n-hexane by distillation under reduced pressures, the reaction mixture was cooled to about 0° C., and then there was added dropwise thereto ethyl bromide (10.9 g, 0.10 mole) at the same temperature over a period of about 1 hour. Thereafter the mixture was heated to 25° C., and the reaction was carried out for another 15 hours at the same temperature.

While maintaining the reaction mixture at the same temperature, there was added thereto a saturated aqueous solution (100 ml) of ammonium chloride, and then water (50 ml) and ethyl acetate (250 ml). After addition of 2N hydrochloric acid to make the aqueous layer acidic, the organic layer was separated, and washed twice with 0.5N hydrochloric acid (80 ml).

After the organic layer was dried over magnesium sulfate (0.2 g), the solvent was removed by distillation under reduced pressures. The residual liquid was distilled under reduced pressures, to provide 7-decynoic acid (13.9 g, 0.083 mole) as a fraction of bp. 95°–98° C./0.1 mmHg in a theoretical yield of 83% based on ethyl bromide used.

EXAMPLES 10–12

A mixture of 1,3-dimethyl-2-imidazolidinone with various promoters indicated in Table 3 was used, and the reaction was carried out otherwise in the same manner as in Example 9, to give 7-decynoic acid in yields shown in Table 3.

TABLE 3

| Examples | Promoters Used (ml/ml) | Theoretical Yields[1] (%) |
|---|---|---|
| 10 | DMI[2]/Ethylenediamine (50/50) | 78 |
| 11 | DMI/Dimethylformamide (50/50) | 73 |
| 12 | DMI/Dimethylformamide | 79 |

TABLE 3-continued

| Examples | Promoters Used (ml/ml) | Theoretical Yields[1] (%) |
|---|---|---|
| | (50/50) | |

Notes:
[1] Based on ethyl bromide.
[2] 1,3-Dimethyl-2-imidazolidinone.

COMPARATIVE EXAMPLES 12-14

Employing promoters as shown in Table 4 in place of 1,3-dimethyl-2-imidazolidinone, the reactions were carried out otherwise in the same manner as in Example 9, to give 7-decynoic acid in theoretical yields shown in Table 4.

TABLE 4

| Comparative Examples | Promoters Used (ml) | Theoretical Yields[1] (%) |
|---|---|---|
| 12 | Ethylenediamine (50) | 51 |
| 13 | Dimethylformamide (50) | 32 |
| 14 | Hexamethylphosphoramide (50) | 66 |

Notes:
[1] Based on ethyl bromide.

EXAMPLE 13

4-Pentyne-1-ol (46.3 g, 0.55 mole) was added dropwise to a pyridine (130 ml) solution of p-toluenesulfonyl chloride (125.8 g, 0.66 mole) below 20° C. over a period of 30 minutes with stirring, and the mixture was stirred at 20°-25° C. for another 5 hours.

After the reaction, water (300 ml) was added to the reaction mixture while maintaining the temperature below 25° C., and then the mixture was extracted twice with ethyl acetate (300 ml). The obtained organic layer was washed with a 0.05N aqueous sulfuric acid solution (100 ml), with a 5% aqueous solution (100 ml) of sodium hydrogen carbonate, and with a saturated aqueous solution of sodium chloride (100 ml) subsequently, followed by drying over magnesium sulfate (30 g), and distillation under reduced pressures, to provide 4-pentyn-1-yl p-toluenesulfonate (128.8 g) with 80.4% purity in a theoretical yield of 79% based on 4-pentyne-1-ol used as a result of a gas chromatographic analysis with a column of 3% OV-17 on Uniport H9 (Shimazu Corp., Japan) provided with a hydrogen flame-ionization detector.

Sodium amide (15.6 g, 0.4 mole) was added to tetrahydrofuran (100 ml) under a nitrogen atmosphere, and then to the sodium amide was added dropwise a tetrahydrofuran (50 ml) solution of 1-(2-tetrahydropyranyloxy)-2-propyne (56.1 g, 0.40 mole) below 25° C. over a period of 20 minutes. Then the mixture was stirred at 45°-50° C. for another 1 hour. After cooling to about 10° C., 1,3-dimethyl-2-imidazolidinone (70 ml) was added to the reaction mixture.

Crude 4-pentyn-1-yl p-toluenesulfonate (59.3 g, or 47.7 g, 0.20 mole as 100% purity compound) dissolved in 1,3-dimethyl-2-imidazolidinone (50 ml) was added dropwise to the above-mentioned sodium acetylide solution below 50° C. over a period of 2 hours, followed by stirring for another 2 hours at temperatures of 20°-25° C.

After the reaction, a 10 W/V % aqueous solution (150 ml) of ammonium chloride was added to the reaction mixture while maintaining the temperature below about 20° C. Then the mixture was extracted twice with ethyl acetate (300 ml). The organic layer was washed twice with water (100 ml), and then with 0.05N aqueous solution (100 ml) of hydrochloric acid, and with a saturated aqueous solution of sodium chloride (100 ml) successively. The organic layer was then removed by distillation under reduced pressures, and the residue was distilled under reduced pressures to provide 1-(2-tetrahydropyranyloxy)-2,7-octadiyne (35.1 g) as a fraction of bp. 107°-112° C./0.3 mmHg in a theoretical yield of 85% based on 4-pentyn-1-yl p-toluenesulfonate used.

COMPARATIVE EXAMPLE 15

Employing N-methylpyrrolidone (50 ml) as a promoter in place of 1,3-dimethyl-2-imidazolidinone, the reaction was carried out otherwise in the same manner as in Example 14, to give 1-(2-tetrahydropyranyloxy)-2,7-octadiyne (25.6 g) in a theoretical yield of 54% based on 4-pentyn-1-yl p-toluenesulfonate used.

What is claimed is:

1. A method of producing substituted acetylenic compounds which comprises: reacting an organic compound having the general formula of $$A-X \qquad (I)$$

wherein A represents a saturated or unsaturated aliphatic hydrocarbon residue of 1-20 carbon atoms which may have one or more substituents inactive in the reaction, and X represents a halogen atom or an arylsulfonyloxy group, with a metal acetylide having the general formula of $$M-C{\equiv}C-B \qquad (II)$$

wherein M represents an alkali metal, and B represents (a) a hydrogen, (b) a saturated or unsaturated hydrocarbon residue which may have one or more substituents inactive in the reaction, or (c) a saturated or unsaturated hydrocarbon residue which has a substituent having the general formula of $$-C{\equiv}C-M \qquad (III)$$

wherein M represents an alkali metal, in the presence of an alkyl-2-imidazolidinone having the general formula of

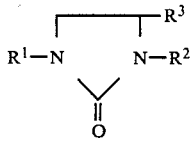

$$(IV)$$

wherein $R^1$ and $R^2$ independently represent a lower alkyl, and $R^3$ represents a hydrogen or a lower alkyl.

2. A method as claimed in claim 1 wherein X is Cl, Br or I.

3. A method as claimed in claim 1 wherein X is a benzenesulfonyloxy or a p-toluenesulfonyloxy group.

4. A method as claimed in claim 1 wherein the alkyls in the alkyl-2-imidazolidinone are independently methyl or ethyl.

5. A method as claimed in claim 1 wherein the alkyl-2-imidazolidinone is 1,3-dimethyl-2-imidazolidinone.

6. A method as claimed in claim 1 wherein the alkyl-2-imidazolidinone is 1,3,4-trimethyl-2-imidazolidinone.

7. A method as claimed in claim 1 wherein the metal in the metal acetylide is Li, Na or K.

* * * * *